United States Patent [19]

Hicks et al.

[11] Patent Number: 4,752,501

[45] Date of Patent: Jun. 21, 1988

[54] METHOD FOR FORMING PATTERNED TIN OXIDE THIN FILM ELEMENT

[75] Inventors: David B. Hicks, Farmington Hills; Adolph L. Micheli, Mt. Clemens; Shih-Chia Chang, Troy, all of Mich.

[73] Assignee: General Motors Corporation, Detroit, Mich.

[21] Appl. No.: 68,545

[22] Filed: Jul. 1, 1987

[51] Int. Cl.$^4$ ............................................... B05D 5/12
[52] U.S. Cl. ................................. 427/126.3; 427/226; 427/272; 427/282
[58] Field of Search .................. 427/126.3, 226, 272, 427/282

[56] References Cited

U.S. PATENT DOCUMENTS 4,370,028  1/1983  Bernhardt ..................... 427/126.3
4,706,493  11/1987  Chang ................................ 73/23

OTHER PUBLICATIONS

Chang et al., IEEE Solid–State Sensors Workshop Technical Digest (1986).

Primary Examiner—Richard Bueker
Attorney, Agent, or Firm—Douglas D. Fekete

[57] ABSTRACT

A method is disclosed for forming a semiconductor tin oxide thin film on a selected region of a surface without forming the film on an adjacent region. An ink film composed of tin(II) carboxylate compound is applied to the surface and heated to partially decompose the compound. A positive photoresist layer is preferably applied to the partially decomposed layer and selectively irradiated to define a mask overlying the selected region. Unwanted photoresist material is dissolved from the adjacent region using an aqueous alkaline solution. It is found that the solution concurrently dissolves the underlying partially decomposed tin compound, without dissolving the compound protected by the mask. Thereafter, the mask is stripped, and the underlying tin compound is heated and further decomposed to produce the desired tin oxide thin film.

4 Claims, 1 Drawing Sheet

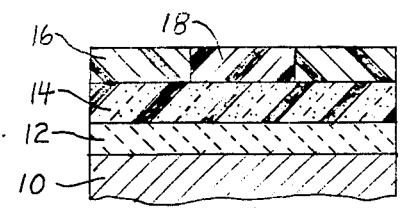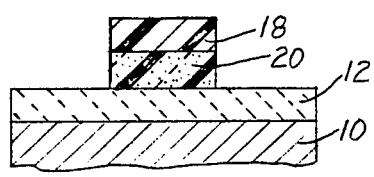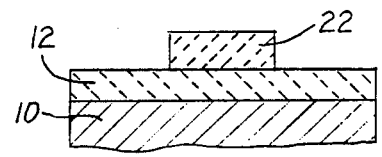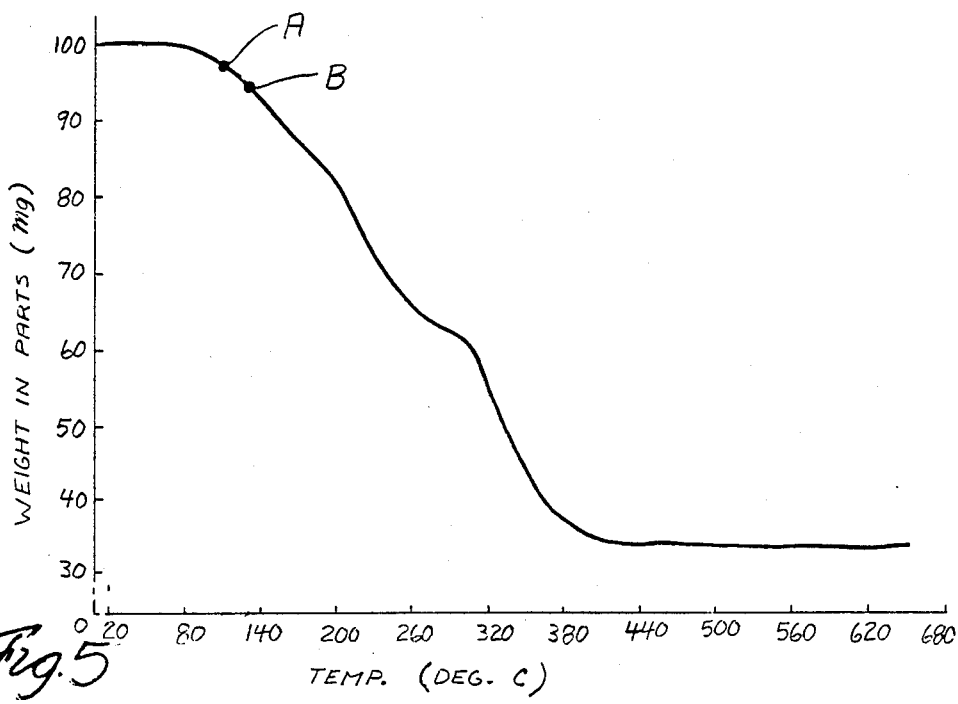

METHOD FOR FORMING PATTERNED TIN OXIDE THIN FILM ELEMENT

BACKGROUND OF THE INVENTION

This invention relates to forming a semiconductor tin oxide thin film element on a selected surface region by thermally decomposing a tin carboxylate compound. More particularly, this invention relates to such method that employs a photoresist mask to define the element and further comprises a pre-mask partial decomposition treatment of the tin compound to allow removal of unwanted tin compound in the same step and with the same solvent as nonmasking photoresist material, without disturbing the masked tin compound, to permit film definition without a separate etching operation.

U.S. patent application Ser. No. 808,546 to Chang et al describes a gas sensor comprising a thin film gas-sensing element composed of a semiconductor tin oxide. The element covers a region of the sensor that is less than the entire surface. The tin oxide film is characterized by a nonstoichiometric, oxygen-deficient composition having a measurable electrical resistivity, the value of which is dependent upon the gas composition. One method for forming a semiconductor tin oxide thin film is by sputter deposition using a tin oxide target. A more convenient method is by metallo-organic deposition (MOD), wherein an ink comprising an organic tin compound, such as tin(II) 2-ethylhexanoate, is applied and fired to form a tin oxide film having the desired composition and gas-sensitive resistivity. Heretofore, the tin oxide is applied to a large surface and etched using a photoresist mask to define the element. A typical mask is formed by applying a photoresist layer and selectively exposing the photoresist layer to light in regions other than the region of the element. The photoresist material is insoluble in aqueous alkaline solution as applied, but becomes soluble upon exposure to light. Thus, following irradiation, nonmask photoresist is washed from the surface using alkaline solvent, leaving the mask. Tin oxide only dissolves slowly in aqueous alkaline solution and thus is removed from unwanted regions in a separate etching operation. After etching, the mask is removed to expose the element.

It is helpful to understanding this invention to recognize that, in a conventional MOD process, the ink is fired prior to applying the mask. The organic tin ink is readily soluble in aqueous alkaline solution. When a photoresist mask is applied to unfired ink, the alkaline solution that removes the nonmask photoresist also washes the ink from the entire surface, including from under the mask.

It has now been found that a partial decomposition treatment of the organic tin compound prior to masking reduces the rate at which the tin material is dissolved by alkaline solution so as to suitably inhibit washing away of masked material, while still allowing removal of nonmasked material.

It is an object of this invention to provide an improved MOD process for producing a semiconductor tin oxide thin film element by thermal decomposition of an organic tin compound, which process comprises a partial decomposition of the tin compound prior to applying and developing a photoresist layer, and which further comprises removal of unwanted tin compound by dissolution in alkaline solvent used to remove nonmask photoresist. Masked regions of the partially decomposed tin compound remain substantially intact despite the solvent. In this manner, the unwanted tin compound is removed in the same step as the nonmask photoresist, thereby eliminating a separate etching step that would otherwise be required to pattern the film.

SUMMARY OF THE INVENTION

In accordance with this invention, an improved MOD method forms a semiconductor tin oxide thin film on a predetermined region of a surface without forming the film on an adjacent region, permitting an element of the oxide film to be formed readily in a desired pattern. In a preferred embodiment, the MOD method comprises applying an ink formed of a thermally decomposable tin carboxylate compound uniformly onto both the pattern region and the adjacent region. The tin ink is heated in air for a time and at a temperature sufficient to partially decompose the compound to produce an intermediate compound having reduced solubility in aqueous alkaline solution of the type used as solvent to remove nonmask photoresist material. The time and temperature of the partial decomposition treatment is dependent upon the particular tin carboxylate. For ink composed of commercial grade tin(II) 2-ethylhexanoate, a preferred partial decomposition step is carried out at a temperature between about 110° C. and 130° C. for a time between about 20 and 30 minutes. For tin(II) neodecanoate ink, a preferred partial decomposition range is between about 240° C. and 245° C. for between about 25 and 30 minutes.

To pattern the partially decomposed tin compound, the film is coated with a photoresist material that is insoluble in an aqueous alkaline solvent. The photoresist layer is selectively exposed to light to produce an insoluble mask overlying the region of the intended element. The photoresist layer is then contacted with aqueous alkaline solvent. In nonmasked regions, the solvent dissolves the photoresist material, and thereafter dissolves the underlying partially decomposed tin compound. In contrast, the mask is not dissolved and protects the underlying tin compound from dissolution. Furthermore, the solvent does not laterally wash away the tin compound underlying the mask, as would occur in the absence of the partial decomposition treatment. In this manner, tin compound remains in the pattern region, but is removed from the adjacent region.

After the unwanted tin compound is removed, the photoresist mask is removed using a suitable nonaqueous solvent to expose the underlying partially decomposed tin compound. The tin compound is then heated in air at a time and for a temperature sufficient to complete decomposition and form a semiconductor tin oxide thin film.

Thus, the method of this invention forms a semiconductor tin oxide thin film only on a predetermined region of a surface, in contrast to present methods that form the tin oxide thin film on an entire surface and thereafter etch to remove tin oxide from unwanted regions. The unwanted tin compound is removed in the same step and using the same solvent as nonmasking photoresist material. However, masked tin compound is not significantly disturbed. Thus, the method of this invention eliminates an expensive and time-consuming etching operation and reduces the number of steps required to form a patterned semiconductor tin oxide thin film element, thereby reducing the time and expense required to manufacture a device such as a gas sensor.

DESCRIPTION OF THE DRAWINGS

The present invention will be further illustrated with reference to the drawings wherein:

FIGS. 1 through 4 schematically depict a sequence of steps for manufacturing a semiconductor tin oxide thin film element in accordance with this invention; and FIG. 5 is a thermogravimetric analysis graph wherein the abscissa indicates temperature and the ordinate indicates weight.

DETAILED DESCRIPTION OF THE INVENTION

Preferred embodiments of this invention are illustrated by the following examples:

EXAMPLE I

In this example, described with reference to FIGS. 1 through 4, a semiconductor tin oxide thin film was formed by thermal decomposition of tin(II) 2-ethylhexanoate compound.

Referring to FIG. 1, a preferred silicon wafer substrate 10 comprises a thermally grown silicon dioxide surface layer 12. An ink was prepared by dissolving one gram tin(II) 2-ethylhexanoate commercially obtained from Alfa Products Division of Morton Thiokol, Inc., into one milliliter ultrapure grade xylene. The ink solution was applied onto layer 12 and uniformly distributed by spinning substrate 10 at about 3,000 RPM for about 120 seconds. The xylene vehicle was allowed to evaporate at ambient temperature, whereupon the ink residue formed a tacky film on the order of 5,000 Å thick. In accordance with this invention, the ink film was heated while exposed to air at about 120° C. for about 30 minutes to produce a partially decomposed film 14 in FIG. 1.

A positive working photoresist material was applied to film 14 and irradiated to produce a layer comprising an alkaline-soluble nonmask portion 16 and alkaline-insoluble mask 18, shown in FIG. 2. A preferred commercial photoresist material was obtained from Shipley Co., Inc., under the trade designation AZ-1350J and comprises an ortho-diazoketone compound dissolved in a vaporizable organic solvent. The commercial liquid was applied to layer 14 and distributed by spinning substrate 10 at about 5000 RPM. Following drying, the photoresist material was prebaked at about 85° C. for about 10 minutes. Nonmask portions 16 of the photoresist layer were selectively exposed to ultraviolet light to convert the photoresist material to a carboxylic acid form soluble in aqueous alkaline solution, without exposing mask 18, so that mask 18 remained in alkaline-insoluble form.

Substrate 10 bearing the irradiated photoresist layer was immersed for about 30 seconds in 0.6 Normal aqueous alkaline solvent obtained from Shipley Co., Inc., under the trade designation Microposit Developer (used undiluted). The alkaline solution dissolved nonmask photoresist 16, but did not dissolve mask 18. In accordance with this invention, the alkaline solution concurrently dissolved the tin compound 14 underlying nonmask photoresist 16. However, the solvent did not significantly erode the partially decomposed tin compound 20 underlying mask 18, as shown in FIG. 3.

Mask 18 was removed by immersion in acetone for about five minutes, thereby exposing film 20. The surface bearing film 20 was heated in air at a temperature of about 500° C. for about one hour to complete decomposition of the tin compound and produce a tin oxide thin film element 22 shown in FIG. 4. The product thin film element 22 is between about 1,000 and 2,000 Å thick and suitable for use as a gas-sensing element.

COMPARATIVE EXAMPLE IA

For comparison, the method of Example I was followed, but without the prepatterning partial decomposition treatment as in the present invention. The tin(II) 2-ethylhexanoate ink was applied in xylene solution and dried. A positive working photoresist layer was applied and irradiated to form a mask, as in Example I. When the substrate bearing the photoresist layer was immersed in alkaline solvent as in Example I, however, the solvent dissolved the ink from the entire surface, including from underneath the mask. The resulting surface was substantially free of tin compound so that no oxide film element could be formed.

COMPARATIVE EXAMPLE IB

For comparison, the method of Example I was followed, but the tin organic compound was fully decomposed prior to applying the photoresist layer. The tin(II) 2-ethylhexanoate was applied in xylene solution, dried and fired in air at about 450° C. for one hour, thereby producing a tin oxide thin film covering the entire substrate surface. A photoresist layer was applied and irradiated as in Example I. The irradiated photoresist layer was immersed in the alkaline solvent used in Example I. Nonmasking photoresist material was dissolved by the solvent, but the tin oxide film was not significantly removed. Thus, additional steps were required to etch the tin oxide thin film from the unmasked substrate surfaces and thereby define the desired element.

EXAMPLE II

In this example, the method of Example I was followed, but utilizing an ink comprising tin(II) neodecanoate compound. Tin(II) neodecanoate was produced by reacting neodecanoic acid and tin ethoxide. Ink was prepared by dissolving 1.0 gram tin(II) neodecanoate in one milliliter xylene. The ink was spun-applied and dried. The dried ink film was partially decomposed by heating in air at a temperature between about 240° C. and 245° C. for about 30 minutes. A photoresist layer was applied and selectively exposed to ultraviolet light to produce a mask, following the steps of Example I. Nonmask photoresist was removed by dissolution using aqueous alkaline solvent. In accordance with this invention, partially decomposed tin compound underlying the exposed photoresist material also was dissolved in the solvent, whereas the partially oxidized tin compound underlying the mask was not significantly disturbed. After removing the mask, the patterned tin compound film was fired in air for about 60 minutes at a temperature of about 450° C. The resulting tin oxide thin film element exhibited satisfactory semiconductive and gas-sensing properties.

Therefore, the improved MOD method of this invention forms a semiconductor tin oxide thin film on a selected region of a surface, without forming the oxide film on adjacent regions, by thermal decomposition of a tin(II) carboxylate compound. Suitable tin(II) compounds are characterized by a molecular formula comprising a tin bonded to an oxygen of a carboxyl group of an organic base portion, as opposed to an organotin compound that comprises a tin-carbon bond. Tin(II)

designates a +2 oxidation state. Thus, the tin is typically bonded to two carboxyl portions. That is, tin(II) 2-ethylhexanoate in Example I comprises two 2-ethylhexanoate groups, as indicated by the formula $Sn(C_8H_{15}O_2)_2$. Tin(II) neodecanoate, as in Example II, is characterized by the formula $Sn(C_{10}H_{19}O_2)_2$. It is believed that tin(IV) compounds, which generally include a halide, do not thermally decompose to an intermediate having suitable solubility for patterning using alkaline solution by the method of this invention.

Upon heating, tin(II) carboxylate compounds decompose to produce a vaporizable organic byproduct and tin oxide. Although decomposition is preferably carried out in air, it is believed, because of the relatively low temperature, that decomposition does not involve reaction with ambient oxygen. Tin(II) carboxylates generally have high solubility in alkaline solution, particularly alkaline solution of the type used to strip nonmasking positive photoresist material, so that the compound is washed away even though underneath a mask, as shown in Comparative Example IA. In contrast, tin oxide derived from the tin organic compound is substantially insoluble in alkaline solution, as shown in Comparative Example IB, so that an etch step is necessary to pattern the tin oxide film once formed.

In accordance with this invention, the tin carboxylate is subjected to a prepatterning partial decomposition treatment to reduce solubility by an amount that allows dissolution of the unmasked film in photoresist developer solvent, while inhibiting dissolution of masked compound. The time and temperature of the prepatterning treatment depends upon the particular ink compound. For a preferred commercial grade tin(II) 2-ethylhexanoate compound in the described embodiments, a suitable treatment comprises 20 to 30 minutes at 110° C. to 130° C. It is found that heating at a temperature less than about 110° C. does not satisfactorily inhibit dissolution of masked film. It is also found that treatment temperatures greater than about 130° C. significantly retard dissolution, undesirably extending the time required to remove the unwanted tin compound using photoresist solvent.

The decomposition behavior of the commercial grade tin(II) 2-ethylhexanoate compound used in Example I is indicated by the thermogravimetric analysis in FIG. 5. Data was obtained using a Thermogravimetric Analyzer obtained from DuPont Corporation under the trade designation Model 9900. A solvent-free sample of the commercial compound was heated from room temperature at a rate of 10° C. per minute in air while continuously weighing the sample. FIG. 5 shows measured sample weight as a function of temperature. Weight loss at temperatures less than about 102° C. is mainly attributed to volatilization of the tin(II) 2-ethylhexanoate compound. At higher temperatures, decomposition of the tin(II) 2-ethylhexanoate compound produces an organic byproduct that vaporizes, resulting in weight loss. It is believed that decomposition proceeds in two stages. During a first stage occurring at temperatures less than about 260° C., the tin(II) 2-ethylhexanoate is believed to decompose to an intermediate tin compound, referred to as a partial oxide. At temperatures above 300° C., weight loss is attributed to further decomposition of the intermediate compound to produce the desired tin oxide. Above about 389° C., minimal further weight loss occurs, indicating a stable tin oxide. A preferred prepatterning temperature range is indicated between points A and B.

A thermogravimetric analysis for the tin neodecanoate compound in Example II is similar to FIG. 5, but at relatively higher temperatures. At temperatures up to about 228° C., weight loss is mainly attributed to volatilization. Above about 228° C., the weight rapidly decreases due to thermal decomposition. Formation of intermediate compound occurs mainly up to about 302° C. Above about 302° C., the intermediate undergoes further decomposition to produce the desired tin oxide. No significant weight change is found above about 420° C., indicating formation of the stable oxide. A preferred prepatterning partial decomposition range is 240° C. to 245° C.

Thus, the temperature range over which a tin(II) carboxylate compound decomposes is dependent upon the particular compound. The decomposition temperature range is also dependent upon impurities in the ink. In Example I, a commercial grade compound, which commenced decomposing at about 102° C., contained sodium in an amount sufficient to produce an oxide film containing 4 weight percent sodium oxide. Thermogravimetric analysis of high purity tin(II) 2-ethylhexanoate compound indicates decomposition commences at about 200° C. The significantly lower decomposition temperature of the commercial material is attributed to the presence of the sodium impurity. Metallo-organic additives, such as platinum compound, blended into the ink to affect gas-sensing properties of the tin oxide film may also affect ink decomposition temperatures. Similarly, an effective temperature for partially decomposing a tin carboxylate compound in accordance with this invention depends upon the particular compound. In general, it is believed that a suitable prepatterning partial decomposition temperature is within a range sufficient to commence decomposition of the compound, but not sufficient to form product oxide; that is, sufficient to produce a reduced solubility intermediate but not decompose the intermediate.

In the Examples, the partially decomposed film was patterned using a positive working photoresist wherein nonmask regions are irradiated to produce a soluble material. However, this invention may also be suitably carried out using a negative working photoresist material, wherein mask regions are irradiated. Nonmask negative photoresist is typically removed by nonaqueous solvent, so that an additional alkaline treatment may be necessary to remove the unwanted tin compound.

Also, although in the Examples unwanted tin compound was dissolved using commercial photoresist developer solvent, other aqueous alkaline solution may be used, for example, potassium hydroxide.

While semiconductor tin oxide thin film elements such as produced by this invention are particularly useful for gas sensing, this invention may be suitably carried out to produce a semiconductor element for other purposes, such as a resistance element for an integrated circuit.

While this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A method for forming a semiconductor tin oxide thin film on a selected region of a surface without forming the film on an adjacent region and such that the film is formed in a desired pattern, said method comprising applying uniformly onto both the selected region and the adjacent region an ink film comprising a thermally decomposable tin(II) carboxylate compound, heating the ink film for a time and at a temperature sufficient to partially decompose the tin carboxylate compound to form a film having reduced solubility in aqueous alkaline solution, coating said partially decomposed film with a photoresist layer such that the selected region carries a photoresist mask insoluble in aqueous alkaline solution, removing the photoresist material from the adjacent region, thereby exposing the underlying partially decomposed tin compound, said partially decomposed compound being protected in the selected region by said mask, dissolving the exposed partially decomposed tin compound using aqueous alkaline solution, whereupon the photoresist mask protects the partially decomposed tin compound in the selected region from dissolution, removing the photoresist material from the selected region to expose the partially decomposed tin compound, and heating the partially decomposed tin compound for a time and at a temperature sufficient to further decompose the compound to produce a semiconductor tin oxide thin film, whereupon the film is formed on the selected region but not on the adjacent region.

2. A method for forming a semiconductor tin oxide thin film on a selected region of a surface without forming the film on an adjacent region and such that the film is formed in a desired pattern, said method comprising applying uniformly onto both the selected region and the adjacent region an ink film comprising a thermally decomposable tin(II) carboxylate compound, heating the ink film in air for a time and at a temperature sufficient to partially decompose the tin compound to form a film having reduced solubility in aqueous alkaline solution, applying a photoresist layer that is essentially insoluble in aqueous alkaline solution onto the partially decomposed tin compound, selectively irradiating the photoresist layer overlying the adjacent region to produce a material that is soluble in aqueous alkaline solvent, whereupon the non-irradiated alkaline-insoluble photoresist material overlying the selected region forms a mask, exposing the surface bearing the irradiated photoresist layer to aqueous alkaline solvent to remove said soluble photoresist material from the adjacent region and to dissolve the underlying partially decomposed tin compound, whereupon the photoresist mask overlying the selected region protects the underlying compound from dissolution, removing the photoresist mask to expose the underlying tin compound, and heating the partially decomposed tin compound for a time and at a temperature sufficient to further decompose the compound to produce a semiconductor tin oxide thin film, whereupon the film is formed on the selected region but not on the adjacent region.

3. A method according to claim 2 wherein the ink film is composed mainly of tin(II) 2-ethylhexanoate and is partially decomposed by heating at a temperature between 110° C. and 130° C. for a time between 20 and 30 minutes.

4. A method according to claim 2 wherein the tin(II) carboxylate compound consists substantially of tin(II) neodecanoate and is partially decomposed by heating at a temperature between about 240° C. and 245° C. for a time between 25 and 30 minutes.

* * * * *